United States Patent [19]
Schenk

[11] 4,439,353
[45] Mar. 27, 1984

[54] ESTERS OF SUBSTITUTED 2,2-DIMETHYLCYCLOHEXANOIC ACID

[75] Inventor: Hanspeter Schenk, Zumikon, Switzerland

[73] Assignee: Givaudan Corporation, Clifton, N.J.

[21] Appl. No.: 326,443

[22] Filed: Dec. 1, 1981

[30] Foreign Application Priority Data

Dec. 10, 1980 [CH] Switzerland ........................ 9103/80
Oct. 14, 1981 [CH] Switzerland ........................ 6573/81

[51] Int. Cl.$^3$ ........................ C07C 69/75; C11B 9/00
[52] U.S. Cl. ........................ 252/522 R; 560/1; 426/538; 131/276
[58] Field of Search ........................ 560/1; 252/522 R; 426/538; 131/276

[56] References Cited

U.S. PATENT DOCUMENTS 3,887,625 6/1975 Schulte-Elte .
4,006,108 2/1977 Ochsner et al. ................ 252/522 R
4,018,718 4/1977 Ochsner et al. ................ 252/522 R
4,113,663 9/1978 Schenk ................ 252/522

OTHER PUBLICATIONS

Shive, J. Am. Chem. Soc., 64, pp. 385-391, (1942).
House, "Modern Synthetic Reactions," 2nd Ed., pp. 1-18, (1972).

*Primary Examiner*—Michael L. Shippen
*Attorney, Agent, or Firm*—Robert F. Tavares

[57] ABSTRACT

Novel substituted 2,2-dimethylcyclohexanoic acid derivatives of the formula:

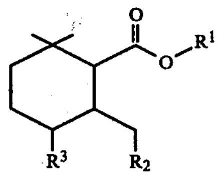

wherein:

$R^1$ represents an alkyl group of one to four carbons;
$R^2$ represents hydrogen or methyl;
$R^3$ represents hydrogen or methyl; but
$R^2$ and $R^3$ are never both hydrogen;

and novel fragrance and flavoring compositions containing same.

12 Claims, No Drawings

ESTERS OF SUBSTITUTED 2,2-DIMETHYLCYCLOHEXANOIC ACID

THE INVENTION

The novel compounds of this invention can be represented by the formula:

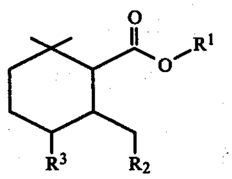

I wherein:

$R^1$ represents an alkyl group of one to four carbons;
$R^2$ represents hydrogen or methyl;
$R^3$ represents hydrogen or methyl; but
$R^2$ and $R^3$ are never both hydrogen.

Formula I is intended to embrace all stereoisomers which are possible considering the possible relative configuration of the substituents at the $C_1$-,$C_2$- and $C_3$-atom in formula I, which may be either cis or trans to one another.

The groups denoted by $R^1$ can be straight-chain or branched-chain. Methyl ethyl and isobutyl are preferred with ethyl being especially preferred.

The mixtures of compounds of formula I in which $R^2$ represents hydrogen and $R^3$ represents methyl with compounds of formula I in which $R^2$ represents methyl and $R^3$ represents hydrogen are preferred. Further, compounds of formula I in which $R^2$ and $R^3$ both represent methyl are preferred.

The invention is also concerned with a process for the manufacture of the compounds of formula I.

This process comprises catalytically hydrogenating an ester of the formula

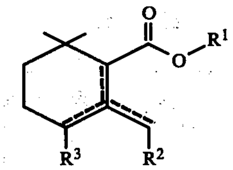

II wherein $R^1$,$R^2$ and $R^3$ have the significance given earlier and one of the dotted lines represents an additional bond.

Suitable catalysts for this process are noble metal catalysts which include, for example, platinum, palladium, ruthenium or rhodium.

The hydrogenation can be carried out with or without the addition of a solvent; inert solvents such as ethyl alcohol, methyl alcohol, cyclohexane etc. are preferred.

The hydrogenation can be carried out at temperatures between, for example, 0° C. and 100° C., especially between 15° C. and 30° C., and at normal pressure or at higher pressures (e.g. 5–20 atmospheres). (H. O. House, Modern Synthetic Reactions, N. A. Benjamin Inc., New York 1972).

According to the process in accordance with the invention, the product of formula I is obtained as a stereo-isomer mixture.

If desired, the separation of the isomer mixture can be carried out in the usual manner, for example, by preparative gas chromatography. The isomers of compounds of formula I do not differ fundamentally in their organoleptic properties, so that on economical grounds especially the isomer mixture can be used.

The preparation of the ester starting materials of formula II can be carried out according to known methods for the preparation of cyclogeranoyl derivatives, for example by cyclizing esters of the formula

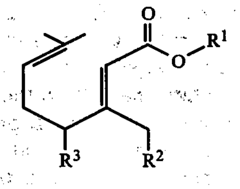

III wherein $R^1$, $R^2$ and $R^3$ have the significance given earlier.

Suitable cyclizing agents are inorganic and organic protonic acids such as sulphuric acid, phosphoric acid, methanesulphonic acid, formic acid, acetic acid etc., or Lewis acids such as boron trifluoride, tin tetrachloride, zinc chloride etc.

The cyclization can be carried out in the presence or absence of a solvent. Suitable solvents are inert solvents such as hexane, benzene, nitromethane etc. The temperature is not critical and the cyclization can be carried out at room temperature or at higher or lower temperatures.

The preparation of the esters of formula III is carried out, for example, when $R^2$ signifies hydrogen and $R^3$ signifies methyl, conveniently from the known 3,6-dimethyl-5-hepten-2-one. For example, this ketone can be reacted with a $C_{1-4}$-carbalkoxy-methylene-diethylphosphonate according to Horner-Wittig [Wadsworth/Emmons modification, J.Amer.Chem.Soc. 83, 1733 [1961]] in the presence of an alkali hydride or alkali alcoholate as the base.

The reaction is conveniently carried out in an aprotic solvent such as benzene, toluene, dimethoxyethane etc. The temperature at which the reaction is carried out is not critical. The temperature range of about 40°–60° C. is preferred, but the reaction can also be carried out at a lower or higher temperature.

The following Reaction Scheme in which $R^1$, $R^2$, $R^3$ and the dotted lines have the significance given earlier illustrates the manufacture of the compounds of formula I:

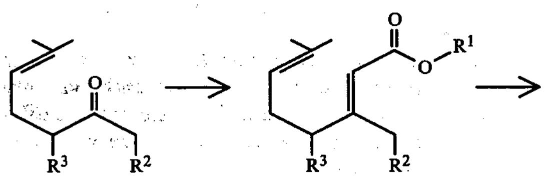

IV III

-continued

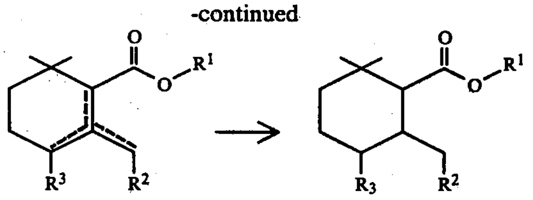

II I

Higher saturated esters of formula I (e.g. those in which $R^1$ signifies propyl or isobutyl) are conveniently manufactured from a methyl or ethyl ester of formula III by trans-esterification, namely in the usual manner by heating with a higher alcohol (e.g. propanol or isobutanol), preferably under alkaline conditions, whereby the methanol or ethanol formed can be distilled off continuously from the reaction mixture.

The compounds I have particular organoleptic properties, on the basis of which they are excellently suited as odorant and/or flavouring substances.

The invention is therefore also concerned with the use of the compounds of formula I as odorant and/or flavouring substances.

On the basis of their natural odour notes the compounds of formula I, especially the mixtures of compounds in which $R^2$ signifies hydrogen and $R^3$ signifies methyl with compounds in which $R^2$ signifies methyl and $R^3$ signifies hydrogen, or the compounds in which $R^2$ and $R^3$ both signify methyl, are suitable, in particular, for modifying known compositions.

The aforementioned mixtures of compounds of formula I in which $R^1$ represents ethyl are distinguished by a powerful, diffuse and very natural-warm top note in a spicy, fruity and woody direction. In addition, a powdery-flowery olfactory aspect is worthy of mention.

The compounds of formula I combine with numerous known natural or synthetic ingredients of odorant compositions, whereby the range of the natural ingredients can embrace not only readily-volatile but also semi-volatile and difficultly-volatile substances, and the range of the synthetic ingredients can embrace representatives from almost all classes of substances, as will be evident from the following compilation:

Natural products such as tree moss absolute, basil oil, bergamotte oil, mandarin oil, mastix absolute, myrtle oil, palmarosa oil, patchouli oil, petitgrain oil (Paraguay) and wormwood oil;

alcohols such as geraniol, linalool, nerol, phenylethyl alcohol, rhodinol and cinnamic alcohol;

aldehydes such as citral, α-methyl-3,4-methylenedioxyhydrocinnamaldehyde, α-hexylcinnamaldehyde, hydroxycitronellal, p-tert. butyl-α-methyl-hydrocinnamaldehyde, p-tert. butyl-α-methyldihydrocinnamaldehyde and methylnonylacetaldehyde;

ketones such as allyl ionone, α-ionone, β-ionone and methyl ionone;

esters such as allyl phenoxyacetate, benzyl salicylate, cinnamyl propionate, dimethylbenzylcarbinyl butyrate, ethyl acetoacetate, linalyl acetate, methyl dihydrojasmonate, styrallyl acetate and vetiveryl acetate;

lactones such as coumarin;

various components often used in perfumery such as mush ambrette, 4-acetyl-6-tert. butyl-1,1-dimethylindane, 1,3,4,6,7,8-hexahydro-4,6,6,7,7,8-hexamethyl-cyclopenta-γ-2-benzopyran, indole, p-methane-8-thiol-3-one and methyleugenol.

Also worthy of mention is the manner in which the compounds of formula I round-off and harmonize the odour notes of known compositions without, however, dominating. Thus, for example, they underline the spicy and herby notes in perfume bases with tea and green character and in rose bases they underline the sought-after character of the heavy, sweet Bulgarian rose which is somewhat reminiscent of "schnaps" (apple brandy).

In fruit bases (e.g. of the apricot type) the aforementioned mixtures can be used effectively to produce a velvety-soft, natural-sweet and rounded-off effect.

The compounds of formula I (or mixtures thereof) can be used in wide limits which, for example, can extend from 0.1% in the case of detergents to 30% in the case of alcoholic solutions. It will be appreciated that these values are not limiting values, since the experienced perfumer can also achieve effects with lower concentrations or can synthesize novel complexes with higher concentrations. The preferred concentrations vary between 0.5 and 25%. The compositions produced with compounds of formula I can be used for all kinds of perfumed consumer goods (Eau-de-Cologne, eau de toilette, essences, lotions, creams, shampoos, soaps, salves, powders, toothpastes, mouth washes, deodorants, detergents, tobacco etc).

The compounds of formula I (or mixtures thereof) can therefore be used in the production of compositions and, as will be evident from the foregoing compilation, using a wide range of known odorant substances or odorant substance mixtures. In the production of such compositions, the known odorant substances or odorant substance mixtures specified earlier can be used according to methods known to the perfumer such as, for example, according to W. A. Poucher, Perfumes, Cosmetics, Soaps 2, 7th Edition, Chapman and Hall, London 1974.

The compounds of formula I or mixtures thereof are likewise excellently suited for use in fruit flavours of various kinds, but especially also for the flavouring of tobacco.

As flavouring substances the compounds of formula I can be used, for example, for the production or improvement, intensification, enhancement or modification of fruit flavours of various kinds (e.g. raspberry or apricot flavours). These flavours can be used, for example, in foodstuffs (yoghurt, confectionery etc.), luxury consumables ("Genussmittel", e.g. tea, tobacco etc.) and drinks (lemonade etc.).

The pronounced flavour qualities of the compounds of formula I (or mixtures thereof) enable them to be used as flavouring substances in low concentrations. A suitable range is, for example, 0.01 ppm–100 ppm, preferably 0.01 ppm–20 ppm, in the finished product (i.e. the flavoured foodstuff, luxury consumable or drink).

In the flavouring of, for example, tobacco, the concentration can, however, also be higher and can have a wider range; for example, a range of 1 ppm–1000 ppm, preferably 50 ppm–500 ppm.

The compounds of formula I can be mixed with the ingredients used for flavouring substance compositions or added to such flavourants in the customary manner. Among the flavourants contemplated in accordance with the present invention there are to be understood flavouring substance compositions which can be diluted or dispersed in edible materials in a manner known per se. They contain, for example, about 0.1–10 weight %, especially 0.5–3 weight %. They can be converted according to methods known per se into the usual forms of use such as solutions, pastes or powders. The products can be spray-dried, vacuum-dried or lyophilized.

The known flavouring substances which are conveniently used in the production of such flavourants are either referred to in the foregoing compilation or can be taken from the relevant literature (see, for example, J. Merory, Food Flavorings, Composition, Manufacture and Use, Second Edition, the Avi Publishing Company, Inc., Westport, Conn. 1968, or G. Fenaroli, Fenaroli's Handbook of Flavor Ingredients, Second Edition, Volume 2, CRC Press, Inc. Cleveland, Ohio, 1975).

For the production of the usual forms of use there can be used, for example, the following carrier materials, thickening agents, flavour-improvers, spices, auxiliary ingredients etc.:

Gum arabic, tragacanth, salts or brewers' yeast, alginates, carrageen or similar absorbents; indole, maltol, dienals, spice oleoresins, smoke flavours, cloves, diacetyl, sodium citrate; monosodium glutamate, disodium inosine-5'-monophosphate (IMP), disodium guanosine-5-phosphate (GMP); or special flavouring substances, water ethanol, propyleneglycol, glycerine.

The following Examples illustrate the present invention.

EXAMPLE 1

30 g of an ester mixture consisting of about 20% of 2,3,6,6-tetramethyl-2-cyclohexene-1-carboxylic acid ethyl ester, about 14% of c,t-2-ethylidene-6,6-dimethylcyclohexane-1-carboxylic acid ethyl ester and about 65% of 2-ethyl-6,6-dimethyl-2-cyclohexene-1-carboxylic acid ethyl ester are dissolved in 300 ml of absolute ethyl alcohol and hydrogenated with the addition of 600 mg of palladium (10% on carbon) while stirring well at normal pressure. 96.9% of the theoretical amount of hydrogen are taken up after 24 hours. The catalyst is filtered off over Celite, back-washed with a small amount of ethanol and the solvent is distilled off on a rotary evaporator.

The crude product (29.8 g) is fractionally distilled over a 10 cm Widmer column in a high vacuum. There are obtained 28 g (92.4% of theory) of a mixture of boiling point 42°–55° C./0.05 mm Hg. In accordance with gas chromatography [glass capillary column (50 m×0.3 mm i.d.) with Ucon HB 5100 as the stationary phase, 140° C. isothermal, helium flow 2.5 ml/minute], the product has essentially the following composition: 41.8% of cis-2-ethyl-6,6-dimethylcyclohexane-1-carboxylic acid ethyl ester, 34.6% of trans-2-ethyl-6,6-dimethylcyclohexane-1-carboxylic acid ethyl ester and 19.6% of 2,3,6,6-tetramethylcyclohexane-1-carboxylic acid ethyl ester (various stereoisomers, inter alia about 4.1% of 1,2 cis-2,3-trans-2,3,6,6-tetramethyl-1-cyclohexanecarboxylic acid ethyl ester and about 9.1% of 1,2 trans-2,3-trans-2,3,6,6-tetramethyl-1-cyclohexane-1-cyclohexanecarboxylic acid ethyl ester). The isomer mixture was separated by means of preparative gas chromatography. The main peaks showed the following spectroscopic data:

Cis-2-ethyl-6,6-dimethyl-cyclohexane-1-carboxylic acid ethyl ester

| IR (liq.): 1735 cm$^{-1}$ | | $^1H$—NMR (360 MHz, $CDCl_3$): | |
|---|---|---|---|
| 0.89 s (3H) | 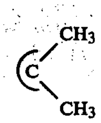 | 1.25 t/7 (3H) | 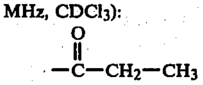 |
| 0.91 t/7 (3H) | $-CH_2-CH_3$ | 2.31 d/4 (1H) | 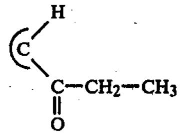 |
| 0.99 s (3H) | 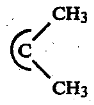 | 4.09 AB—part of ABX$_3$ (2H) | 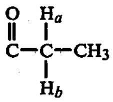 |

Trans-2-ethyl-6,6-dimethyl-cyclohexane-1-carboxylic acid ethyl ester

| IR (liq.): 1735 cm$^{-1}$ | | $^1H$—NMR (360 MHz, $CDCl_3$): | |
|---|---|---|---|
| 0.86 t/7 (3H) | $-CH_2-CH_3$ | 1.26 t/7 (3H) | 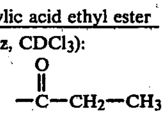 |
| 0.93 s (3H) | 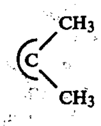 | 1.89 d/11.5 (1H) | 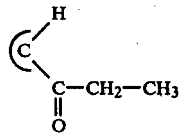 |
| 0.97 s (3H) | 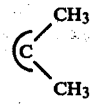 | 4.13 q/7 (2H) | 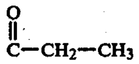 |

1,2-Cis, 2,3-trans, 2,3,6,6-tetramethyl-1-cyclohexane-carboxylic acid ethyl ester

| IR (liq.): 1725 cm$^{-1}$ | | $^1H$—NMR (360 MHz, $CDCl_3$): | |
|---|---|---|---|
| 0.86 d/7 (3H) | $C_3-CH_3$ | 1.40–1.60 m (2H) i.a. | $C_2-H_{ax}$ |

-continued

| | | | |
|---|---|---|---|
| 0.87 d/t (3H) | $C_2-CH_3$ | 1.68-1.81 m (1H) | $C_3-H_{ax}$ |
| 0.89 s (3H) | $C_6(CH_3)_2$ | 1.84-1.95 m (1H) | $C_5-H_{ax}$ |
| 0.99 s (3H) | | 2.22 d/s (1H) | $C_1-H_{eq}$ |
| 1.25 t/7 (3H) | $\overset{O}{\overset{\|\|}{C}}-CH_2-CH_3$ | 4.10 q/7 (2H) | $\overset{O}{\overset{\|\|}{C}}-CH_2-CH_3$ |

1,2-Trans, 2,3-trans-2,3,6,6-tetramethyl-1-cyclohexane-carboxylic acid ethyl ester

| IR (liq.): 1725 $cm^{-1}$ | | $^1H$—NMR (360 MHz, $CDCl_3$): | |
|---|---|---|---|
| 0.84 d/6 (3H) | $C_3-CH_3$ | 1.26 t/7 (3H) | $\overset{O}{\overset{\|\|}{C}}-CH_2-CH_3$ |
| 0.925 s (3H) | $C_6-CH_3$ | 1.87 d/7 (1H) | $C_1-H_{ax}$ |
| 0.93 d/6 (3H) | $C_2-CH_3$ | 4.14 q/7 (2H) | $\overset{O}{\overset{\|\|}{C}}-CH_2-CH_3$ |
| 0.95 s (3H) | $C_6-CH_3$ | | |

The starting material is prepared as follows:

To a cooled solution of 5.8 g (0.252 g of atom) of sodium in 130 ml of absolute ethanol is added dropwise at a temperature of 5°-10° C. a solution of 30 g (0.214 mol) of a ketone mixture consisting of 20% of 3,6-dimethyl-5-hepten-2-one and 80% of 7-methyl-6-octen-3-one and 62.4 g (0.278 mol) of phosphonoacetic acid triethyl ester in 130 ml of absolute toluene. Subsequently, the mixture is left to come to room temperature and to react-out overnight. The mixture is poured into ice-water and extracted three times with hexane. The combined hexane solutions are washed neutral with sodium chloride solution, dried over sodium sulphate and evaporated. The crude product (43 g) is fractionally distilled in a high vacuum over a 10 cm Widmer column. There are obtained 28.9 g (64.3%) of a mixture of boiling point 58°-61° C./0.02 mm Hg; $n_D^{20}=1.4708$. The mixture consists of 20% of c,t-3,4,7-trimethyl-2,6-octadienoic acid ethyl ester and 80% of c,t-3-ethyl-7-methyl-2,6-octadienoic acid ethyl ester.

228 ml of formic acid are cooled to 0°-5° C. At this temperature there are added 12 ml of concentrated sulphuric acid and subsequently the mixture is stirred for 1 hour. To the resulting acid mixture there are cautiously added dropwise at +5° C. 24 g of the foregoing ester mixture consisting of 20% of c,t-3,4,7-trimethyl-2,6-octadienoic acid ethyl ester and 80% of c,t-3-ethyl-B 7-methyl-2,6-octadienoic acid ethyl ester. After completion of the addition, the mixture is left to come to room temperature and it is stirred at this temperature for a further 1 hour. The mixture is poured onto ice and extracted three times with hexane. The combined hexane solutions are washed neutral once with water, twice with sodium bicarbonate solution and finally twice with water, dried over sodium sulphate and evaporated. The crude product (22.5 g) is fractionally distilled in a high vacuum on a 10 cm Widmer column. There are obtained 17 g (70.8%) of an ester mixture consisting of about 20% of 2,3,6,6-tetramethyl 2-cyclohexene-1-carboxylic acid ethyl ester, 14% of c,t-2-ethylidene-6,6-dimethyl-cyclohexane-1-carboxylic acid ethyl ester and 65% of 2-ethyl-6,6-dimethyl-2-cyclohexene-1-carboxylic acid ethyl ester of boiling point 102° C./6 mm Hg; $n_D^{20}=1.4626$.

EXAMPLE 2

22.4 g (0.1 mol) of an ester mixture consisting of about 80% of 2-ethyl-3,6,6-trimethyl-2-cyclohexene-1-carboxylic acid ethyl ester (remainder: double bond isomers) are dissolved in 250 ml of absolute ethyl alcohol and hydrogenated with the addition of 800 mg of palladium (10% on carbon) in an autoclave at 10 bar and 60° C. for 24 hours. The catalyst is filtered off over Celite, backwashed with a small amount of ethyl alcohol and the solvent is distilled off on a rotary evaporator.

The crude product (21.8 g) is fractionally distilled over a 5 cm Widmer column in a high vacuum. There are obtained 18.0 g (79.6% of theory) of a mixture of boiling point 80°-81°/0.15 mm Hg; $n_D^{20}=1.4527$. In a capilliary gas chromatogram (50 m×0.31 mm i.d., Ucon HB 5100, 140° C. isothermal, helium flow 2.5 ml/minute, split ratio 1:30) there are visible four peaks with the following percentage amounts of the total mixture (listed according to increasing retention time):

| | |
|---|---|
| $P_1$ | 42.4% |
| $P_2$ | 34.9% |
| $P_3$ | 16.5% |
| $P_4$ | 6.2% |

Peaks 1,2,3 and 4 represent the four possible stereoisomers of 2-ethyl-3,6,6-trimethyl-cyclohexane-1-carboxylic acid ethyl ester.

The peak-1 product was separated by preparative gas chromatography and showed the following spectroscopic properties:

| IR (liq.): 1735 $cm^{-1}$ | | $^1H$—NMR (360 MHz, $CDCl_3$): | |
|---|---|---|---|
| 0.87 d/7 (3H) | $C_3-CH_3$ | 1.35 t/7 (2H) | $-\overset{O}{\overset{\|\|}{C}}-CH_2-CH_3$ |

-continued

| IR (liq.): $1735\ cm^{-1}$ | | $^{1}H$—NMR (360 MHz, $CDCl_3$): | |
|---|---|---|---|
| 0.90 s (3H) | 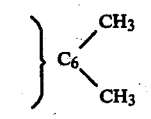 | 2.44 d/5 (1H) | $C_1$—H |
| 0.99 s (3H) | | 4.1 m (2H) | 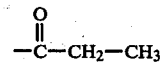 |
| 0.91 t/7 (2H) | $C_2—CH_2—CH_3$ | | |

Odour: woody, fruity-berry like, camphorous, reminiscent of eucalyptus seeds, aromatic.

EXAMPLE 3

5 g of an ester mixture consisting of about 90% of 2-ethyl-6,6-dimethyl-2-cyclohexene-1-carboxylic acid ethyl ester (remainder: double bond isomers) are dissolved in 50 ml of absolute ethyl alcohol and hydrogenated with 100 mg of palladium (10% on carbon) while stirring vigorously at normal pressure and at room temperature for 24 hours. The catalyst is filtered off over Celite, back-washed with a small amount of ethyl alcohol and the solvent is distilled off on a rotary evaporator. The crude product (4.9 g) is distilled in a bulb-tube. There are obtained 4.3 g (85.2% of theory) of a mixture of boiling point 65° C./0.08 mm Hg. From a capilliary gas chromatogram (50 m×0.31 mm i.d. with Ucon HB 5100, 140° C. isothermal, helium flow 2.5 ml/minute, split ratio 1:30) the following composition results: about 47% of cis-2-ethyl-6,6-dimethyl-1-cyclohexanecarboxylic acid ethyl ester and about 50% of trans-2-ethyl-6,6-dimethyl-1-cyclohexanecarboxylic acid ethyl ester. (Spectroscopic data: see Example 1).

Odour: very natural in the direction of camomile and tagetes.

EXAMPLE 4

10 g of an ester mixture consisting of about 21% of 2,3,6,6-tetramethyl-2-cyclohexene-1-carboxylic acid isobutyl ester, about 12% of c,t-2-ethylidene-6,6-dimethyl-cyclohexane-1-carboxylic acid isobutyl ester and about 61% of 2-ethyl-6,6-dimethyl-2-cyclohexene-1-carboxylic acid isobutyl ester are dissolved in 75 ml of absolute ethyl alcohol and hydrogenated with the addition of 300 mg of palladium (5% on carbon) in an autoclave at 10 bar and 50% C for 15 hours. The catalyst is filtered off over Celite, back-washed with a small amount of ethyl alcohol and the solvent is distilled off on a rotary evaporator.

The crude product (9.9 g) is fractionally distilled over a 5 cm Vigreux column in a high vacuum. There are obtained 8.2 g (85.4% of theory) of a mixture of boiling point 67°-68° C./0.09 mm Hg; $n_D^{20}=1.4510$. In accordance with gas chromatography [glass capilliary column (50 m×0.3 mm i.d.) with Ucon HB 5100 as the stationary phase, 140° C. isothermal, helium flow 2.5 ml/minute], the product has essentially the following composition: 55.1% of cis-2-ethyl-6,6-dimethyl-cyclohexane-1-carboxylic acid isobutyl ester, 31,2% of trans-2-ethyl-6,6-dimethyl-cyclohexane 1-carboxylic acid isobutyl ester and 13.7% of 2,3,6,6-tetramethyl-1-cyclohexanecarboxylic acid isobutyl ester (various stereoisomers).

Odour: flowery, somewhat fatty, herby.

The starting material is prepared as follows:

To a solution of 140 mg of sodium in 101.3 g of isobutyl alcohol is added dropwise a solution of 27 g of a mixture consisting of about 20% of c,t-3,4,7-trimethyl-2,6-octadienoic acid ethyl ester and about 80% of c,t-3-ethyl-7-methyl-2,6-octadienoic acid ethyl ester (prepared as described in Example 1) in 135 g of cyclohexane. The mixture is heated to boiling and thereby the cyclohexane is distilled off, whereby the distilled-off amount is replaced continuously from a dropping funnel (about 250 ml in 4 hours). The mixture is washed neutral with water (3 times), dried over sodium sulphate and evaporated.

The crude product (29.4 g) is fractionally distilled over a 15 cm Widmer column in a high vacuum. There are obtained 27.5 g (70.9% of theory) of a mixture of boiling point 80°-82° C./0.04 mm Hg; $n_D^{20}=1.4660$. The mixture consists of about 20% of c,t-3,4,7-trimethyl-2,6-octadienoic acid isobutyl ester and about 80% of c,t-3-ethyl-7-methyl-2,6-octadienoic acid isobutyl ester. This mixture is cyclized in a manner analogous to that described in Example 1. There is thus obtained in 68.9% yield a mixture of boiling point 64°-66° C./0.04 mm Hg; $n_D^{20}=1.4608$. The mixture consists of about 21% of 2,3,6,6-tetramethyl-2-cyclohexene-1-carboxylic acid isobutyl ester, about 12% of c,t-2-ethylidene-6,6-dimethyl-cyclohexane-1-carboxylic acid isobutyl ester and about 61% of 2-ethyl-6,6-dimethyl-2-cyclohexene-1-carboxylic acid isobutyl ester.

In the following Examples "mixtures I" stands for the product of Example 1.

EXAMPLE 5

Perfumery base with tea character

| | Parts by weight |
|---|---|
| Dipropyleneglycol | 500 |
| Linalool extra | 70 |
| Methyleugenol | 50 |
| p-Menthane-8-thiol-3-one [10% in dipropyleneglycol (DPG)] | 50 |
| Mandarin oil | 50 |
| Myrtle oil | 50 |
| Petitgrain oil | 40 |
| β-Ionone | 30 |
| Basil oil | 20 |
| α-Methyl-3,4-methylenedioxy-hydro-cinnamaldehyde | 20 |
| Allyl phenoxyacetate | 10 |
| Indole (10% in DPG) | 10 |
| | 900 |

By adding 100 parts by weight of mixture I the composition becomes substantially more diffuse and more powerful. It also becomes fresher, more spicy and sweeter and receives, subliminally, a flowery character in the direction of rose.

If the composition is dissolved in ethyl alcohol and tested sensorily in a concentration range which is usual for eau de toilette, namely 5-10 weight %, then the composition containing the mixture I also exhibits after several hours on smelling strips an extraordinary diffusion with at the same time very warm radiance. This effect is very desirable, but rather unusual for a substance which is actually relatively readily volatile.

EXAMPLE 6

Green base

| | Parts by weight |
|---|---|
| Citral | 10 |
| Wormwood oil | 10 |
| Mastrix absolute | 20 |
| Basil oil | 80 |
| Methyl dihydrojasmonate | 100 |
| Linalyl acetate | 200 |
| α-Hexylcinnamaldehyde | 200 |
| Benzyl salicylate | 200 |
| Ethyl alcohol (95°) | 130 |
| | 950 |

The addition of 50 parts by weight of mixture I to the foregoing green base intensifies the herby-green and spicy aspects of the composition in a remarkable manner, which is ascertained especially by means of freshly dipped smelling strips. The impression of the balanced form, combined with flowery-salicylate like notes upon smelling the stored smelling strips is very strongly reminiscent of anthranilate odorant substances. The composition, not only fresh but also stored, now becomes more powerful and has a greatly increased diffusion.

EXAMPLE 7

Composition with rose character

| | Parts by weight |
|---|---|
| Phenylethyl alcohol | 465 |
| Geraniol synthetic | 80 |
| Cinnamic alcohol (substitute) | 70 |
| Nerol | 65 |
| Cinnamyl propionate | 55 |
| 4-Acetyl-6-tert.butyl-1,1-dimethylindane | 10 |
| Dipropyleneglycol | 155 |
| | 900 |

By adding 100 parts by weight of mixture I the rose character of the original composition clearly becomes warmer and softer, and the diffusion increases. Moreover, a clear damascone note appears. In the bottom the dominating musk character is slightly softened and pleasantly rounded-off.

EXAMPLE 8

Composition with apricot character

| | Parts by weight |
|---|---|
| α-Ionone | 160 |
| Dimethylbenzylcarbinyl butyrate | 100 |
| Ethyl acetyl-acetate | 60 |
| 1,3,4,6,7,8-Hexahydro-4,6,6,7,8,8-hexamethyl-cyclopenta-γ-2-benzopyran) | 50 |
| Undecalactone | 30 |
| Palmarosa oil | 40 |
| Allyl ionone | 40 |
| Dipropyleneglycol | 500 |
| | 980 |

By adding 20 parts by weight of mixture I the apple-like weak green note of the original composition and its musk note are advantageously altered to the desired apricot note. The composition containing mixture I is clearly more natural, more harmonic and less rough. In particular, in the bottom the influence of the addition is clearly noticeable in that previously non-harmonizing elements of the composition are now combined with one another very harmonically and at the same time the musk character, which is less desired here, is suppressed.

EXAMPLE 9

Composition (chypre)

| | Parts by weight |
|---|---|
| Styrallyl acetate | 20 |
| Methylnonylacetaldehyde [aldehyde $C_{12}$—MNA] (10% in diethyl phthalate) | 20 |
| Vetiveryl acetate | 50 |
| Rhodinol (citronellol-geraniol mixture) | 50 |
| Patchouli oil | 50 |
| Tree moss absolute (50% in diethyl phthalate) | 50 |
| p-Tert.butyl-α-methylhydrocinnamaldehyde | 100 |
| Hydroxycitronellal | 100 |
| Methyl ionone | 100 |
| Musk ambrette | 100 |
| Coumarin | 100 |
| Bergamotte oil | 100 |
| | 900 |

The addition of 100 parts by weight of mixture I confers to freshly dipped smelling strips a very pleasant fruity note, so that the novel composition becomes substantially warmer and softer without being obtrusive. In the bottom, unpleasant soapy-like and troublesome notes, above all of the aldehyde $C_{12}$-MNA, are advantageously enveloped.

EXAMPLE 10

Apricot flavour

| | Parts by weight | |
|---|---|---|
| Linalyl acetate (10% in ethanol) | 0.3 | 0.3 |
| Cinnamaldehyde (10% in ethanol) | 0.4 | 0.4 |
| Geraniol | 0.5 | 0.5 |
| Angelica root oil | 0.5 | 0.5 |
| Amyl butyrate | 1.0 | 1.0 |
| Amyl valerate | 1.0 | 1.0 |
| Vanillin | 2.0 | 2.0 |
| γ-Nonalactone | 2.0 | 2.0 |
| Petitgrain oil (Paraguay) | 2.0 | 2.0 |
| Benzaldehyde | 2.5 | 2.5 |
| Orange oil | 5.0 | 5.0 |
| γ-Undecalactone | 15.0 | 15.0 |
| Ethanol | 967.8 | 947.8 |
| Mixture I (10% in ethanol) | — | 20.0 |
| | 1.000.0 | 1.000.0 |

By adding mixture I to the foregoing apricot composition its fruity note is intensified quite clearly. The fruity note now becomes fuller and more rounded-off and, moreover, there appears a velvety-soft note which is reminiscent of fully ripe apricots.

I claim:

1. A compound of the formula

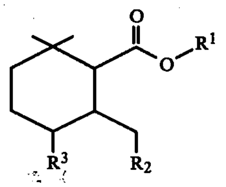

I wherein:

$R^1$ represents an alkyl group of one to four carbons;

$R^2$ represents hydrogen or methyl;

$R^3$ represents hydrogen or methyl; but $R^2$ and $R^3$ are never both hydrogen.

2. A compound according to claim 1 wherein $R^2$ and $R^3$ both represent methyl.

3. A compound according to claim 1 wherein $R^1$ is ethyl, $R^2$ is methyl and $R^3$ is methyl.

4. A compound according to claim 2 wherein $R^1$ is ethyl.

5. A compound according to claim 1 wherein $R^1$ is ethyl, $R^2$ is methyl and $R^3$ is hydrogen.

6. A composition consisting essentially of a mixture of compounds having the formulae

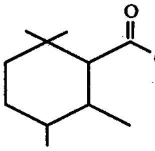

and

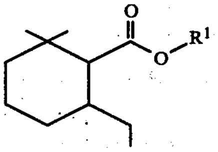

wherein $R^1$ represents an alkyl group of one to four carbons.

7. A composition in accordance with claim 6, wherein $R^1$ represents ethyl.

8. A composition in accordance with claim 6, wherein $R^1$ represents isobutyl.

9. A fragrance and/or flavoring composition comprising an effective amount of a compound of the formula

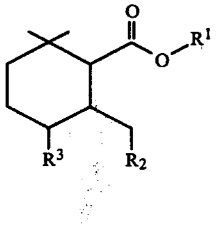

I wherein:

$R^1$ represents an alkyl group of one to four carbons;

$R^2$ represents hydrogen or methyl;

$R^3$ represents hydrogen or methyl; but $R^2$ and $R^3$ are never both hydrogen and at least one other fragrance and/or flavoring substance.

10. A fragrance and/or flavoring composition in accordance with claim 9 comprising an effective amount of a mixture of compounds having the formula

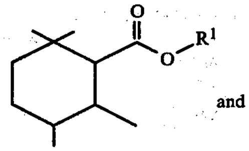

and

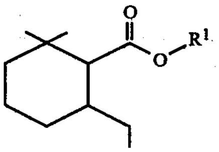

wherein $R^1$ represents an alkyl group of one to four carbons.

11. A composition in accordance with claim 9 or 10 wherein $R^1$ represents ethyl.

12. A composition in accordance with claim 9 or 10 wherein $R^1$ represents isobutyl.

* * * * *